United States Patent
Hama

(10) Patent No.: US 11,798,655 B2
(45) Date of Patent: Oct. 24, 2023

(54) FEATURE VECTOR FEASIBILITY ESTIMATION

(71) Applicant: INTERNATIONAL BUSINESS MACHINES CORPORATION, Armonk, NY (US)

(72) Inventor: Toshiyuki Hama, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1197 days.

(21) Appl. No.: 16/412,732

(22) Filed: May 15, 2019

(65) Prior Publication Data

US 2020/0365235 A1    Nov. 19, 2020

(51) Int. Cl.
*G16C 20/10* (2019.01)
*G06N 3/08* (2023.01)
*G06F 16/901* (2019.01)
*G16C 20/70* (2019.01)
*G16C 20/20* (2019.01)
*G16C 20/80* (2019.01)

(52) U.S. Cl.
CPC ......... *G16C 20/10* (2019.02); *G06F 16/9024* (2019.01); *G06N 3/08* (2013.01); *G16C 20/20* (2019.02); *G16C 20/70* (2019.02); *G16C 20/80* (2019.02)

(58) Field of Classification Search
CPC ........ G16C 20/10; G16C 20/20; G16C 20/70; G16C 20/80; G16C 60/00; G16C 20/50; G06F 16/9024; G06N 3/08; G06N 5/02
See application file for complete search history.

(56) References Cited

U.S. PATENT DOCUMENTS

| | | |
|---|---|---|
| 2013/0252280 A1 | 9/2013 | Weaver et al. |
| 2017/0116371 A1* | 4/2017 | Dimon ................. G16B 40/20 |
| 2017/0193200 A1 | 7/2017 | Hsu et al. |
| 2022/0406416 A1* | 12/2022 | Muthiah Ravinson ..................... G06N 3/0985 |

FOREIGN PATENT DOCUMENTS

| | | |
|---|---|---|
| CN | 102930113 A | 2/2013 |
| CN | 109033738 A | 12/2018 |
| CN | 109461475 A | 3/2019 |
| WO | 2015002860 A1 | 1/2015 |
| WO | 2018227167 A1 | 12/2018 |

OTHER PUBLICATIONS

International Search Report issued in PCT Application No. PCT/IB2020/054518, dated Aug. 25, 2020, pp. 1-9.
Bombarelli et al., "Automatic Chemical Design Using a Data-Driven continuous Representation of Molecules", arXiv:1610.02415v3. Dec. 5, 2017. pp. 1-26.
Fei et al., "Structure Feature Selection for Chemical Compound Classification", 2008 8th IEEE International Conference on BioInformatics and BioEngineering 2008. Oct. 8, 2008. pp. 1-6.
J. Mclaughlin, "On connected degree sequences", arXiv preprint arXiv:15:11. Nov. 30, 2015. pp. 1-7.

* cited by examiner

*Primary Examiner* — Xiao En Mo
(74) *Attorney, Agent, or Firm* — Tutunjian & Bitetto, P.C.; Robert Richard Aragona

(57) ABSTRACT

Feature vector feasibility is estimated by generating a target structure vector that represents numbers of a plurality of partial structures, from a feature vector of a molecule candidate, determining whether a molecule structure of the molecule candidate is feasible by using at least the target structure vector.

25 Claims, 11 Drawing Sheets

Feature Vector

| Data-Driven Feature Section | Pre-defined Building Component Counts Section |
|---|---|

410      420

400

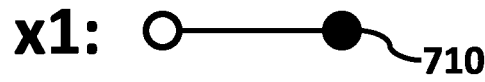
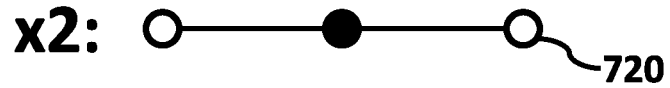
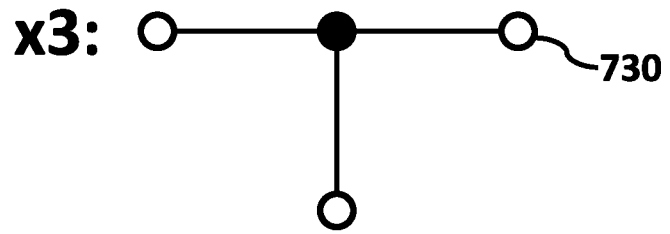
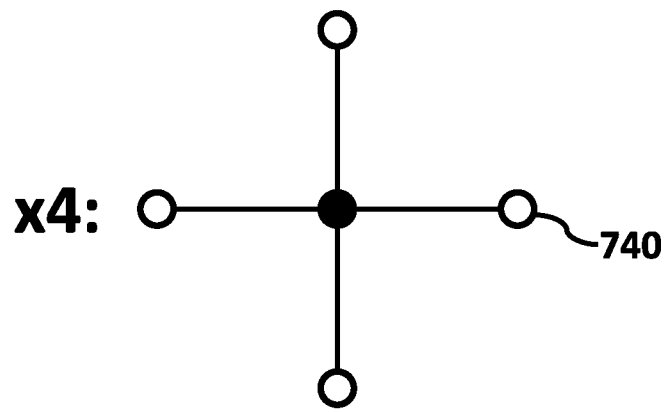
FIG. 7
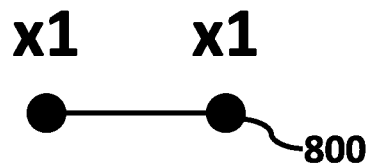
FIG. 8

| Label | Action | Operation to SV | Condition |
|---|---|---|---|
| α1 (a+b1) | Add node to x1 | +(0,1,0,0) | |
| α2 (a+b2) | Add node to x2 | +(1,-1,1,0) | |
| α3 (a+b3) | Add node to x3 | +(1,0,-1,1) | |
| β11 (b1+b1) | Add edge to x1-x1 | +(-2,2,0,0) | sum1 >= 3 AND sum2 >=1 |
| β12 (b1+b2) | Add edge to x1-x2 | +(-1,0,1,0) | sum1 >= 4 AND sum2 >= 2 |
| β22 (b2+b2) | Add edge to x2-x2 | +(0,-2,2,0) | sum2 >= 4 |
| β13 (b1+b3) | Add edge to x1-x3 | +(-1,1,-1,1) | sum1 >= 5 AND sum2 >= 2 |
| β23 (b2+b3) | Add edge to x2-x3 | +(0,-1,0,1) | sum1 >= 5 AND sum2 >= 3 |
| β33 (b3+b3) | Add edge to x3-x3 | +(0,0,-2,2) | sum2 >= 5 |

Ring Creation Action (brace grouping β rows)

sum1 = x1+x2+x3+x4
sum2 = x2+x3+x4

FIG. 9

| Label | Base Action | Operation to SV |
|---|---|---|
| a | New node | +(1,0,0,0) |
| b1 | Edge to x1 (b1) | +(-1,1,0,0) |
| b2 | Edge to x2 (b2) | +(0,-1,1,0) |
| b3 | Edge to x3 (b3) | +(0,0,-1,1) |

FIG. 10

| Number of nodes | Number of Rings | Structure Vector |
|---|---|---|
| 2 | 0 | (2, 0, 0, 0) |
| 3 | 0 | (2, 1, 0, 0) |
| 4 | 0 | (2, 2, 0, 0) |
| 4 | 0 | (3, 0, 1, 0) |
| 4 | 1 | (0, 4, 0, 0) |
| ⋮ | ⋮ | ⋮ |
| 50 | ... | ... |
FIG. 12
(a) 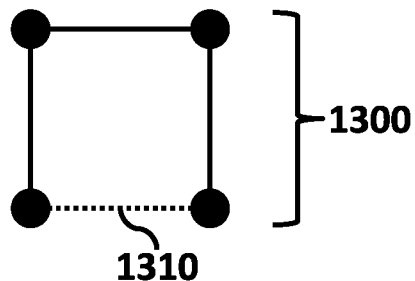  (b) 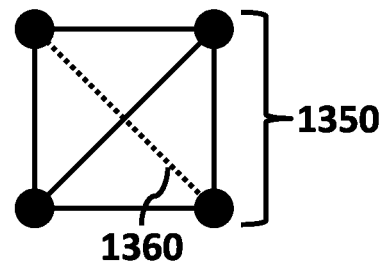
FIG. 13
| Ring Creating Actions (#ring) | 0 ring | 1 ring | 2 ring | 3 ring | 4 ring | 5 ring | ... |
|---|---|---|---|---|---|---|---|
| Range of Actual Rings | [0,0] | [1,1] | [2,2] | [3,4] | [4,6] | [5,8] | |
FIG. 14

FEATURE VECTOR FEASIBILITY ESTIMATION

BACKGROUND

Technical Field

The present invention relates to feature vector feasibility estimation.

Description of the Related Art

Information technology can be used to search for new materials that satisfy target properties. However, inefficiencies exist that can be costly in terms of time and money.

SUMMARY

According to an aspect of the present invention, provided is a computer-implemented method, including generating a target structure vector that represents numbers of a plurality of partial structures, from a feature vector of a molecule candidate, determining whether a molecule structure of the molecule candidate is feasible by using at least the target structure vector. According to this aspect, the infeasible feature vectors may be identified and thus reducing the amount of computational resources and time needed for material discovery.

According to another aspect of the present invention, optionally provided is the method of the preceding aspect, the plurality of partial structures including: a first structure having one edge connected to the one node, a second structure having two edges connected to the one node, a third structure having three edges connected to the one node, and a fourth structure having four edges connected to the one node. According to this aspect, the feasibility of feature vector may be accurately determined with 4 types of partial structures.

According to another aspect of the present invention, optionally provided is the method of the preceding aspect, further including: acquiring a number of atoms and a number of rings of the molecule candidate from the feature vector of the molecule candidate, wherein the determining whether a molecule structure of the molecule candidate is feasible by using at least the target structure vector is performed by further using the number of atoms and the number of rings of the molecule candidate. According to this aspect, the feasibility of feature vectors may be accurately determined with information of the number of atoms and rings in the molecule candidate.

The foregoing aspect may also include an apparatus configured to perform the computer-implemented method, and a computer program product storing instructions embodied on a computer-readable medium or programmable circuitry, that, when executed by a processor or the programmable circuitry, cause the processor or the programmable circuitry to perform the computer-implemented method. The summary clause does not necessarily describe all features of the embodiments of the present invention. Embodiments of the present invention may also include sub-combinations of the features described above.

BRIEF DESCRIPTION OF THE DRAWINGS

FIG. 7 shows the plurality of partial structures according to an embodiment of the present invention.

FIG. 8 shows the initial graph and a corresponding structure vector according to an embodiment of the present invention.

FIG. 9 shows operation vectors of actions according to an embodiment of the present invention.

FIG. 10 shows operation vectors of base actions according to an embodiment of the present invention.

FIG. 12 shows stored structure vectors for pairs of numbers of nodes and rings according to an embodiment of the present invention.

FIG. 13 shows ring creation actions according to an embodiment of the present invention.

FIG. 14 shows a range of a number of rings with ring creation actions according to an embodiment of the present invention.

DETAILED DESCRIPTION

Hereinafter, example embodiments of the present invention will be described. The example embodiments shall not limit the invention according to the claims, and the combinations of the features described in the embodiments are not necessarily essential to the invention.

Figure 1:
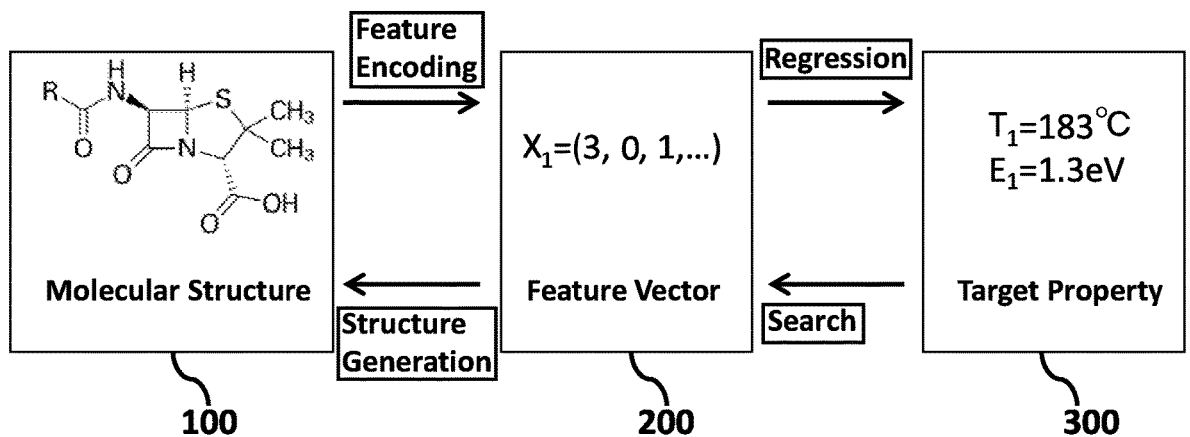
FIG. 1 shows an exemplary framework, according to an embodiment of the present invention.

FIG. 1 shows an exemplary framework, according to an embodiment of the present invention. In the framework, a molecule structure 100 is transformed into a feature vector 200, which may be a latent representation of the molecule structure, by feature encoding. A regression model is trained from the feature vector 200 and a property of the molecule structure 100, such that the regression model predicts properties of the molecule structure 100 from the feature vector 200.

Then a feature vector 200 that gives a target property 300 may be found by using the trained regression model. In an embodiment, a promising feature vector fv may be found by solving a numerical optimization problem for minimizing the difference of target property values $V_p$ and estimated property values by the regression model f as shown in the following equation (1).

$$fv = \mathrm{argmin}_{v \in S} |V_p - f(v)| \quad (1)$$

A promising molecular structure may be generated from the feature vector fv by using a molecular generator. It may sometimes be impossible to generate a molecular structure from the found feature vector. In order to save computational resources and time for obtaining the promising molecule structure, a regressor may eliminate infeasible feature vectors from search space S in equation (1). Hereinafter an apparatus for identifying infeasible feature vectors will be described.

Figure 2:
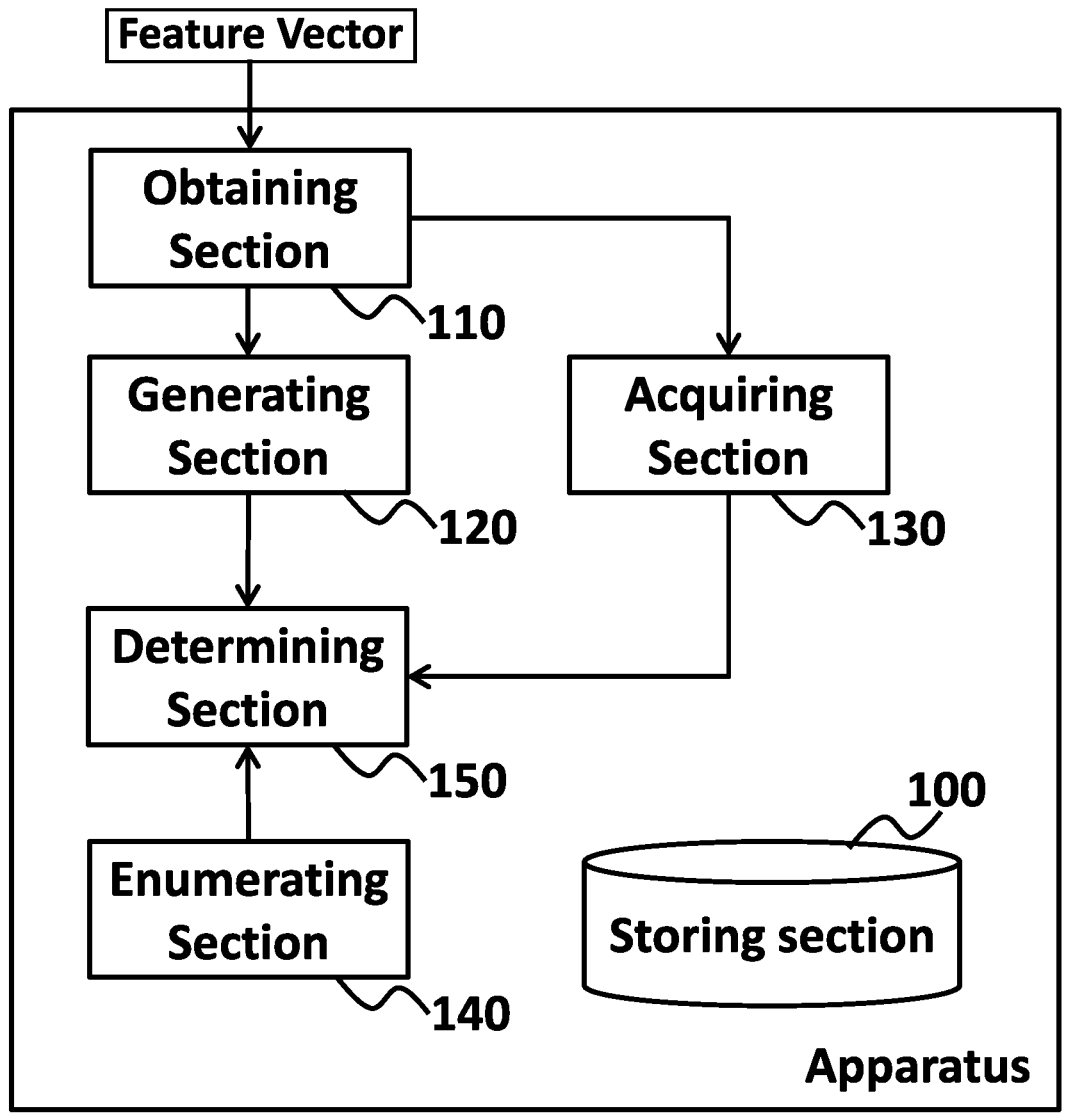
FIG. 2 shows an exemplary configuration of an apparatus 10, according to an embodiment of the present invention.

FIG. 2 shows an exemplary configuration of an apparatus 10, according to an embodiment of the present invention. The apparatus 10 may identify infeasible feature vectors, which cannot be converted into molecule structures. Thereby, the apparatus 10 may reduce the amount of computational resources and/or time to obtain promising molecule structures.

The apparatus 10 may include a processor and/or programmable circuitry. The apparatus 10 may further include one or more computer readable mediums collectively including instructions. The instructions may be embodied on the computer readable medium and/or the programmable circuitry. The instructions, when executed by the processor or the programmable circuitry, may cause the processor or the programmable circuitry to operate as a plurality of operating sections.

Thereby, the apparatus 10 may be regarded as including a storing section 100, an obtaining section 110, a generating section 120, an acquiring section 130, an enumerating section 140, and a determining section 150.

The storing section 100 stores information used for the processing that the apparatus 10 performs. The storing section 100 may also store a variety of data/instructions used for operations of the apparatus 10. One or more other elements in the apparatus 10 (e.g., the obtaining section 110, the generating section 120, the acquiring section 130, the enumerating section 140, and the determining section 150) may communicate data directly or via the storing section 100, as necessary.

The storing section 100 may be implemented by a volatile or non-volatile memory of the apparatus 10. In some embodiments, the storing section 100 may store one or more feature vectors, a table including structure vectors, the number of atoms and/or rings of a molecule candidate, and other data related thereto.

The obtaining section 110 obtains a feature vector of a molecule candidate. In an embodiment, the obtaining section 110 may obtain the feature vector from a regressor which may be implemented by the apparatus 10 or another apparatus. The feature vector may include a plurality of elements and may indicate various characteristics of the molecule candidate.

In an embodiment, the feature vector may be defined at least partially in an automatic data-driven manner, such as a convolutional neural network. In another embodiment, it may be preliminary defined at least partially by human experience and/or knowledge. Details of the feature vector are explained below.

The obtaining section 110 may obtain other data necessary for operations of the apparatus 10. The obtaining section 110 may provide the generating section 120 and the acquiring section 130 with the feature vector. In an embodiment, the feature vector may represent the numbers of substructures in the molecule candidate. Details of the feature vector are explained below.

The generating section 120 may generating a target structure vector from the feature vector of the molecule candidate. The target structure vector may represent numbers of a plurality of partial structures in the molecule candidate. In an embodiment, the generating section 120 may extract a finger print of the molecule candidate from the feature vector, as the target structure vector.

The generating section 120 may further generate one or more secondary structure vectors that are larger than the target structure vector. The generating section 120 may provide the determining section 140 with the target structure vector and/or the one or more secondary structure vectors.

The acquiring section 130 may acquire a number of atoms and a number of rings of the molecule candidate from the feature vector of the molecule candidate. The acquiring section 130 may further acquire a number of atoms of the molecule candidate for each valence, from the feature vector of the molecule candidate. The acquiring section 130 may provide the determining section 150 with the acquired information.

The enumerating section 140 may enumerate feasible structure vectors. In an embodiment, the enumerating section 140 may enumerate feasible structure vectors for each pair of the number of nodes and rings. In an embodiment, the enumerating section 140 may be implemented in another apparatus outside the apparatus 10, and may preliminarily prepare feasible structure vectors. The enumerating section 140 may provide the enumerated feasible structure vectors with the determining section 150 directly or via the storing section 100.

The determining section 150 may determine whether a molecule structure of the molecule candidate is feasible by using at least the target structure vector. In an embodiment, the determining section 150 may further use the one or more secondary structure vectors that is equal to or larger than the target structure vector for determining the feasibility.

In some embodiments, feasible can be defined as possible for manufacture or can exist in a stable form. When a molecule candidate is feasible, the molecule can be possibly manufactured or exist the natural world. When a molecule candidate is infeasible, the molecule candidate cannot be manufactured or cannot exist in the natural world.

In an embodiment, the determining section 150 may further use the number of atoms and the number of rings of the molecule candidate for determining the feasibility. In an embodiment, the determining section 150 may further use the number of atoms of the molecule candidate for each valence for determining the feasibility.

The determining section 150 may determine that the molecule structure of the molecule candidate is feasible in response to the target structure vector being included in a preliminary defined space.

In an embodiment, the determining section 150 may determine that the molecule structure of the molecule candidate is feasible in response to the target structure vector being included in a preliminary defined space that corresponds to the number of atoms and the number of rings of the molecule candidate.

The preliminary defined space may be defined by the feasible structure vectors enumerated by the enumerating section 140. In an embodiment, the preliminary defined space corresponding to the number of atoms and the number of rings of the molecule candidate is defined by the enumerated feasible structure vectors.

Figure 3:
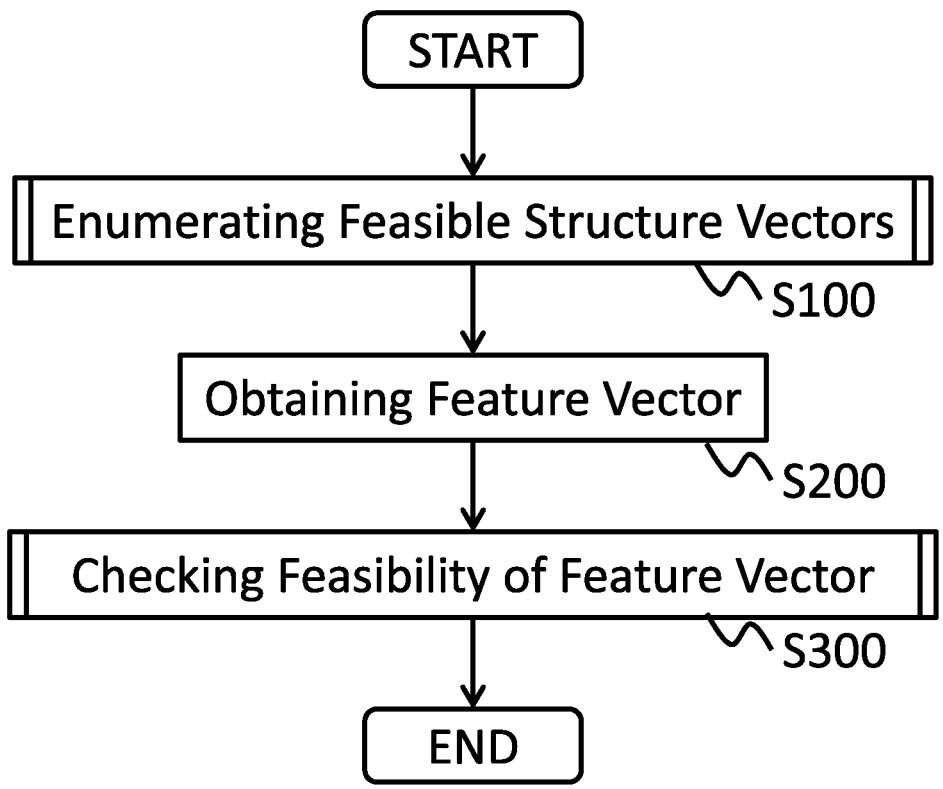
FIG. 3 shows an operational flow according to an embodiment of the present invention.

FIG. 3 shows an operational flow according to an embodiment of the present invention. The present embodiment describes an example in which an apparatus, such as the apparatus 10, performs operations from S100 to S300, as shown in FIG. 3, to check feasibility of a feature vector of a molecule candidate.

At S100, an enumerating section such as the enumerating section 140 may enumerate feasible structure vectors. Details of the operation of S100 are further described with respect to FIG. 6.

At S200, an obtaining section such as the obtaining section 110 may obtain a feature vector of a molecule candidate. The feature vector may include an indication of whether the molecule candidate includes one or more unit structures. The feature vector may also indicate a number of atoms and a number of rings in the molecule candidate. Hereinafter, the feature vector of the molecule candidate may be referred to as "target feature vector."

At S300, an apparatus, such as the apparatus 10 in FIG. 2, may check feasibility of the feature vector of the molecule candidate. The apparatus section may use the feasible structure vectors prepared at S100 and the feature vector obtained at S200. Details of the operation of S300 are further described with respect to FIG. 15.

Figures 4, 5:
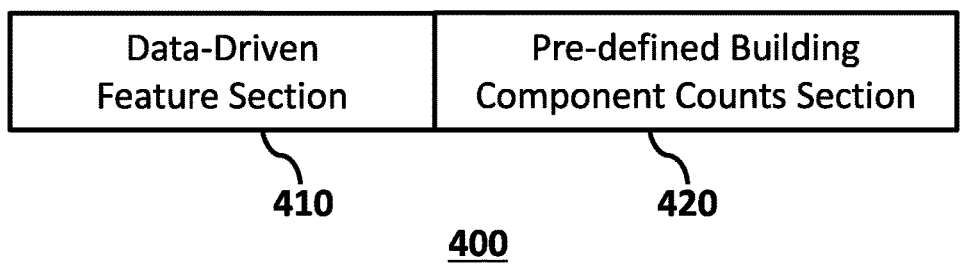
FIG. 4 shows a feature vector 400 according to an embodiment of the present invention.
FIG. 5 shows substructures according to an embodiment of the present invention.

FIG. 4 shows a feature vector 400 according to an embodiment of the present invention. In an embodiment, the feature vector 400 may include a data-driven feature section 410 and a pre-defined building component counts section 420. In an embodiment, the feature vector 400 may be a concatenation of the data-driven feature section 410 and the pre-defined building component counts section 420.

The data-driven feature section 410 may represent a number of unit structures of the molecule. Thereby, the data-driven feature section 410 may represent a structure of the molecule by ignoring differences of atoms and/or bonds.

Here an example of a definition of the feature vector is explained. Let $M=\{m_1, m_2, \ldots, m_N\}$ represent a set of molecular structures in a given dataset for molecular candidates. Any molecular structure may include a set of smaller unit structures (which may be also referred to as "substructures") represented as $S=\{s_1, s_2, \ldots\}$.

This means that by regarding a molecular structure and a substructure as graphs composed of nodes (atoms) and edges (chemical bonds), s can be a partial graph of m. For a molecule of $n^{th}$ sample $m_n$, a set of substructures composing the molecule may be represented as $S^{(n)}=\{s_1, s_2, \ldots\}$. Here, it may be assumed that $S^{(n)}$ is an exhaustive set included in $m_n$. That is, $S^{(n)}$ may incorporate all the substructures, of which the minimum is an atom and the maximum is the molecule itself, and therefore may be the complete collection of substructures included in the molecule $m_n$.

Next we count the number of substructures in a molecule. Let $N_D(m, s)$ denote the count of s appearing in m. An example of a molecule $m_n$, a set of substructures $S^{(n)}$, and counts of them $N_D(m_n, S_i^{(n)})$ is shown in FIG. 5. In FIG. 5, hydrogen (H) and carbon (C) atoms are not explicitly depicted, and substructures are partially shown. An exhaustive set of substructures $S^{FULL}$ for a given molecules set M may be created. This set is obtained by a below equation (2)

$$S^{Full}=U_{i=1}^{N}S^{(i)} \quad (2),$$

where N denotes number of molecules' samples. Expanding elements of $S^{FULL}$ as $S_1^{FULL}, S_2^{FULL} \ldots$, and using the definition of $N_D(m, s)$, we define a vector for a molecule $m_n$ by a below equation (3)

$$x_D^{(n)}=(N_D(m_n,S_1^{Full}),N_D(m_n,S_2^{Full}),\ldots) \quad (3).$$

From its definition, $x_D^{(n)}$ represents topological features of a molecular structure by incorporating counts of all partial graphs appearing in $m_n$, but due to the exhaustiveness, its information includes substantial redundancy. For example, most of the substructures in $S^{FULL}$ appear only once or a few times, even in the full molecules set M; therefore, using them all may not be suitable.

In order to select only the substructures that affect the target property, feature selection on it may be performed. Denoting the target property as y, a LASSO (Least Absolute Shrinkage and Selection Operator) regression model L: $x_D \to y$ may be created. Tuning the hyper parameter (degree of $L_1$ penalty term) and setting threshold $w_{th}$ for absolute value of regression coefficient |W|, the system may select important substructures. We denote the set of selected substructures $S^{Select}$ corresponding feature vector as=$x_D^{Select}$. $x_D^{Select}$ may be used as the data-driven feature section 410 of the feature vector in the molecule candidate. In an embodiment, $S^{Select}$ may only include small structure that include few atoms (e.g., 4-5 atoms) at most as the substructures.

The pre-defined building component counts section 420 may include information about building components of the molecule candidate. In an embodiment, the pre-defined building component counts section 420 may include information of backbone, atoms, and/or bonds of the molecule candidate.

The information of backbone may include a number of heavy atoms and n-membered rings (e.g., polygons with n side) in the molecule candidate. The heavy atoms may be atoms other than hydrogen (H), and may correspond to nodes represented in a graph.

The information of atoms may include a number of specific atoms, such as oxygen (O), nitrogen (N), Sulphur (S), etc. The information of atoms may further include a number of carbon (C) atoms. The information of atoms may further include a number of hydrogen (H) atoms.

In an embodiment, the information of bonds may include a number of double bonds and triple bonds. In an embodiment, the information of bonds may further include a number of rings, such as a number of alicyclic rings and/or a number of aromatic rings.

Figure 6:
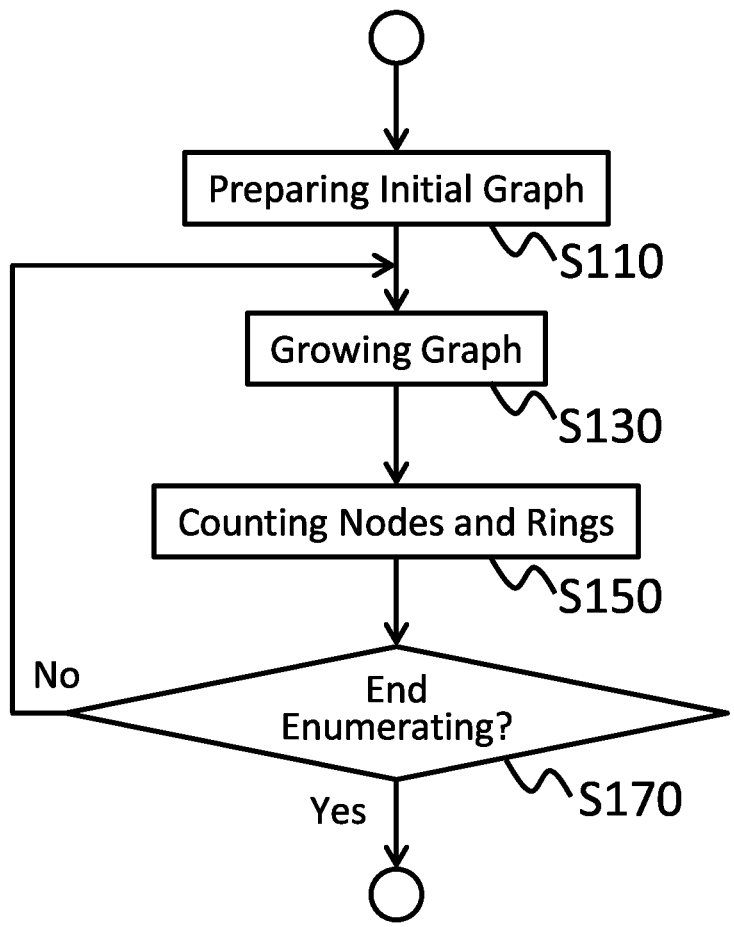
FIG. 6 shows a sub-flow of S100 in the flow of FIG. 3 according to an embodiment of the present invention.

FIG. 6 shows a sub-flow of S100 in the flow of FIG. 3 according to an embodiment of the present invention. An enumerating section, such as the enumerating section 140, may perform operations of S110-S170 of FIG. 6 at the operation S100 of FIG. 3.

At S110, the enumerating section 140 may prepare a structure vector of an initial graph. The initial graph may include two nodes and one edge connecting the two nodes.

The structure vector may represent the numbers of a plurality of partial structures in the initial graph. The partial structures may be finger structures. In an embodiment, the plurality of partial structures may include structures having different numbers of edges connected to a node.

In a specific embodiment, the plurality of partial structures may include a first structure having one edge connected to the one node, a second structure having two edges connected to the one node, a third structure having three edges connected to the one node, and a fourth structure having four edges connected to the one node.

FIG. 7 shows the plurality of partial structures according to an embodiment of the present invention. In FIG. 7, the plurality of partial structures include the first structure 710, the second structure 720, the third structure 730, and the fourth structure 740. A central node (shown by a black dot) in the first structure 710 may be referred to as x1, a central node (shown by a black dot) in the first structure 720 may be referred to as x2, a central node (shown by a black dot) in the first structure 730 may be referred to as x3, and a central node (shown by a black dot) in the first structure 740 may be referred to as x4.

The structure vector of a graph may be represented as a vector $(x_1, x_2, x_3, x_4)$, where $x_1$ represents a number of nodes classified as the central node of x1 in the graph, $x_2$ represents a number of nodes classified as the central node of x2 in the graph, $x_3$ represents a number of nodes classified as the central node of x3 in the graph, and x4 represents a number of nodes classified as the central node of x4 in the graph.

FIG. 8 shows the initial graph and a corresponding structure vector according to an embodiment of the present invention. As shown in FIG. 8, the initial graph 800 includes two nodes, both of which can be regarded as the central node in x1 in FIG. 7. Therefore, the enumerating section may provide the structure vector (2, 0, 0, 0) of the initial graph 800.

At S110, the enumerating section may count the number of nodes and the number of rings of the initial graph. The initial graph 800 in FIG. 8 can be regarded as including two nodes. The initial graph 800 does not include a ring. Therefore, the enumerating section may count "2" as the number of nodes and "0" as rings of the initial graph 800.

After the operation of S110, the enumerating section may iterate a loop of S130-S170. Thereby the enumerating section may develop a graph from the initial graph.

At S130, the enumerating section may grow a graph. The enumerating section may add a new node to the graph, and/or form a new ring in the graph for growing the graph.

In an embodiment, the enumerating section may grow a graph by performing an action to a structure vector of the graph. Hereinafter, a graph to be grown may be referred to as "target graph", and a structure vector of the target graph may be referred to as "target structure vector." In an embodiment, the enumerating section may add an operation vector to the target structure vector to grow the target graph.

FIG. 9 shows operation vectors of actions according to an embodiment of the present invention. An operation vector of the action labelled as "α1" may correspond to an action of adding a node to the central node in x1 (which may be referred to as "x1 node") and may be represented as (0, 1, 0, 0). When adding a new node to the x1 node of the target graph, the enumerating section may add (0, 1, 0, 0) to the target structure vector.

Similarly, an operation vector of the action labelled as "α2" may correspond to an action of adding a node to the central node in x2 (which may be referred to as "x2 node") and may be represented as (1, −1, 1, 0), an operation vector of the action labelled as "α3" may correspond to an action of adding a node to the central node in x3 (which may be referred to as "x3 node") and may be represented as (1, 0, −1, 1).

An operation vector of the action labelled as "β11" may correspond to an action of adding an edge between two x1 nodes, and may be represented as (−2, 2, 0, 0). When adding an edge between two x1 nodes in the target graph, the enumerating section may add (−2, 2, 0, 0) to the target structure vector.

Similarly, an operation vector of the action labelled as β12" may correspond to an action of adding an edge between an x1 node and an x2 node and may be represented as (−1, 0, 1, 0). An operation vector of the action labelled as β22" may correspond to an action of adding an edge between two x2 nodes and may be represented as (0, −2, 2, 0).

An operation vector of the action labelled as "β13" may correspond to an action of adding an edge between an x1 node and an x3 node and may be represented as (−1, 1, −1, 1). An operation vector of the action labelled as "β23" may correspond to an action of adding an edge between an x2 node and an x3 node and may be represented as (0, −1, 0, 1). An operation vector of the action labelled as "β33" may correspond to an action of adding an edge between two x3 nodes and may be represented as (0, 0, −2, 2).

FIG. 10 shows operation vectors of base actions according to an embodiment of the present invention. The actions listed in FIG. 9 may be decomposed into base actions labeled "a", "b1", "b2", and "b3" shown in FIG. 10. For example, action "α1" may be decomposed into base actions "a" and "b1." In other words, operation vector α1 (0, 1, 0, 0) is equal to a sum of an operation vector of "a" (1, 0, 0, 0) and an operation vector of "b1" (−1, 1, 0, 0).

Similarly, action "α2" may be decomposed into base actions "a" and "b2", and action "α3" may be decomposed into base actions "a" and "b3." Actions "β11"-"β33" can be decomposed into combinations of "b1"-"b3" as shown in FIG. 9.

Figure 11:
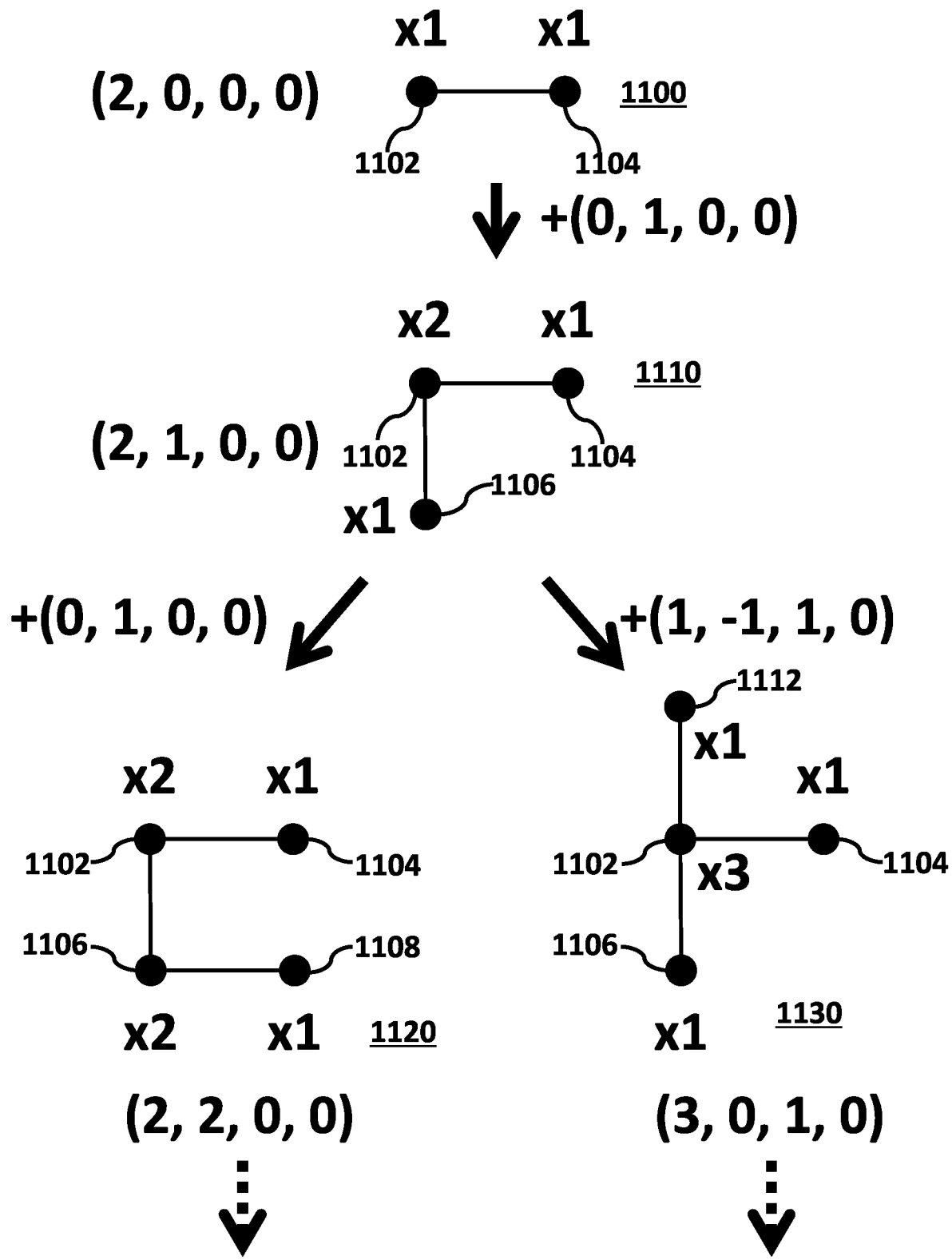
FIG. 11 shows an exemplary growing process according to an embodiment of the present invention.

FIG. 11 shows an exemplary growing process according to an embodiment of the present invention. In the embodiment of FIG. 11, the enumerating section may generate graphs 1110, 1120, 1130, . . . from an initial graph 1100 by operations of S130 in iterations of the loop of S130-S170.

For example, at a first operation of S130, the enumerating section may generate a new graph 1110 from the initial graph 1100 by adding an operation vector of the action α1 (0, 1, 0, 0) to a structure vector of the initial graph 1100 (2, 0, 0, 0) to obtain a structure vector (2, 1, 0, 0) of the graph 1110. This operation amounts to adding a new node to a node x1 in the initial graph 1100.

In an embodiment, at a second operation of S130, the enumerating section may generate a new graph 1120 from the graph 1110 by adding an operation vector of the action α1 (0, 1, 0, 0) to a structure vector of the graph 1110 (2, 1, 0, 0) to obtain a structure vector (2, 2, 0, 0) of the graph 1120. This operation amounts to adding a new node to a node x1 in the graph 1110.

In an embodiment, at a third operation of S130, the enumerating section may generate a new graph 1130 from the graph 1110 by adding an operation vector of the action a2 (1, −1, 1, 0) to a structure vector of the graph 1110 (2, 1, 0, 0) to obtain a structure vector (3, 0, 1, 0) of the graph 1130. This operation amounts to adding a new node to a node x2 in the graph 1110.

In an embodiment, at a fourth operation of S130, the enumerating section may generate a new graph (not shown) from the graph 1110 by adding an operation vector of the action (311 (−2, 2, 0, 0) to a structure vector of the graph 1110 (2, 1, 0, 0) to obtain a structure vector (0, 3, 0, 0) of the new graph. This operation amounts to adding a new edge to two nodes x1 in the graph 1110.

The enumerating section may further grow the graphs 1120, 1130, . . . by adding an operation vector selected from the actions listed in FIG. 9. The enumerating section may select actions such that a calculated structure vector does not include a negative value. For example, when the target structure vector is (2, 1, 0, 0), the enumerating section may not select an action α3, of which operation vector is (1, 0, −1, 1).

The enumerating section may select actions so as to ensure that a ring is created by the selected action. In an embodiment, the enumerating section may select an action only when a condition corresponding to the action is met. The conditions for the actions are shown in FIG. 9. For example, when the target structure vector is (2, 1, 0, 0), the enumerating section may not select an action (312, of which condition includes $x_1+x_2+x_3+x_4>=4$ AND $x_2+x_3+x_4>=2$.

At S150, the enumerating section may count nodes and rings in a graph grown at the most recent S130, which may be hereinafter referred to as a "grown graph."

In an embodiment, the enumerating section may count a number of nodes by calculating $x_1+x_2+x_3+x_4$ for the grown graph $(x_1, x_2, x_3, x_4)$. In an embodiment, the enumerating section may count a number of ring creating actions (actions β11-β33 in FIG. 9) selected so far, as a number of rings. In another embodiment, the enumerating section may count a number of rings by calculating $1-\frac{1}{2}(x_1-x_3-2x_4)$ for the grown graph $(x_1, x_2, x_3, x_4)$.

At S150, the enumerating section may further store a structure vector of the grown graph for a pair of the counted number of nodes and the counted number of rings of the grown graph. For example, when a grown graph is a graph 1120 in FIG. 11, the enumerating section may store a structure vector (2, 2, 0, 0) for a number of node "4" and a number of ring "0."

FIG. 12 shows stored structure vectors for pairs of numbers of nodes and rings according to an embodiment of the present invention. The enumerating section may store structure vectors for corresponding pairs of the number of nodes and rings during iterations of S130-S170.

As shown in FIG. 12, the enumerating section may store a structure vector (2, 0, 0, 0) for a number of nodes (which may be hereinafter referred to as "#node") of 2 (corresponding to the graph 1100), and for a number of rings (which may be hereinafter referred to as "#ring") of 0. The enumerating section may store a structure vector (2, 1, 0, 0) for #node 3 and #ring 0 (corresponding to the graph 1110), a structure vector (2, 2, 0, 0) for #node 4 and #ring 0 (corresponding to the graph 1120), a structure vector (3, 0, 1, 0) for #node 4 and #ring 0 (corresponding to the graph 1130), and a structure vector (0, 4, 0, 0) for #node 4 and #ring 1.

In an embodiment, the enumerating section may iterate the operations of S130-S170 so as to generate all possible graphs within a given size (e.g., 50 nodes). In an embodiment, the enumerating section may iterate the operations of S130-S170 so as to generate a part of all possible graphs within the given size.

In an embodiment, the enumerating section may store a structure vector for a pair of #node and a modified #ring. When the enumerating section performs ring creation action (e.g., (322 in FIG. 9), sometimes two rings may be added to a target graph. However, #ring may be counted based on SSSR (Smallest Set of Smallest Rings) and may not reflect an actual number of rings in a grown graph.

FIG. 13 shows ring creation actions according to an embodiment of the present invention. As shown in FIG. 13(a), an edge 1310 has been added to a target graph 1300, of which structure vector is (2, 2, 0, 0) by a ring creation action β11. With this action, one ring is added to the target graph 1300.

Meanwhile an edge 1360 has been added to a target graph 1350, of which structure vector is (0, 2, 2, 0) by a ring creation action (322 as shown in FIG. 13 (b). With this single action, two rings are added to the target graph 1350. Therefore, an exact number of rings in a grown graph may not be determined by only counting a number of ring creation actions.

FIG. 14 shows a range of a number of rings with ring creation actions according to an embodiment of the present invention. As shown in FIG. 14, when 1 ring creation action is performed, a grown graph has 1 ring. When 2 ring creation actions are performed, a grown graph has 2 rings. When 3 ring creation actions are performed, a grown graph has 3 rings or 4 rings. When 4 ring creation actions are performed, a grown graph has 4 rings, 5 rings, or 6 rings. When 5 ring creation actions are performed, a grown graph has 5-8 rings.

In an embodiment, the enumerating section may preliminary store a table as shown in FIG. 14. In another embodiment, the enumerating section may calculate a range of the number of rings.

In an embodiment, the enumerating section may store a structure vector for a pair of #node and each of a possible #ring. For example, when a structure vector of a grown graph is (0, 0, 4, 0), #node is 4 and #ring (e.g., counts of ring creation action) is 3, the enumerating section may store the structure vector (0, 0, 4, 0) for both of a pair of #node 4 and #ring 3 and a pair of #node 4 and #ring 4.

At S170, the enumerating section may determine whether to end the operation of S100. In an embodiment, the enumerating section may determine whether it is possible to grow a graph within a predetermined size of graph (e.g., within 50 #node). The enumerating section may determine to end S100 in response to determining that it is impossible to grow a graph within a predetermined size of graph. In an embodiment, the enumerating section may determine whether a predetermined amount of time has passed after starting the operation of S100.

In response to determining not to end the operation of S100, the enumerating section may go back to the operation of S130 to iterate a loop of S130-S170. In an embodiment, at a next operation of S130, the enumerating section may grow a target graph in accordance with a width-first search (e.g., growing the target graph so as not to increase #node as long as possible) according to an embodiment. In another embodiment, the enumerating section may grow a target graph in accordance with a depth-first search (e.g., growing the target graph so as to increase #node as long as possible) according to another embodiment.

After the iterations of S130-S170, the enumerating section may store structure vectors such as shown in FIG. 9. The stored structure vectors are used as preliminary defined space at the operation of S300 as explained below.

Figure 15:
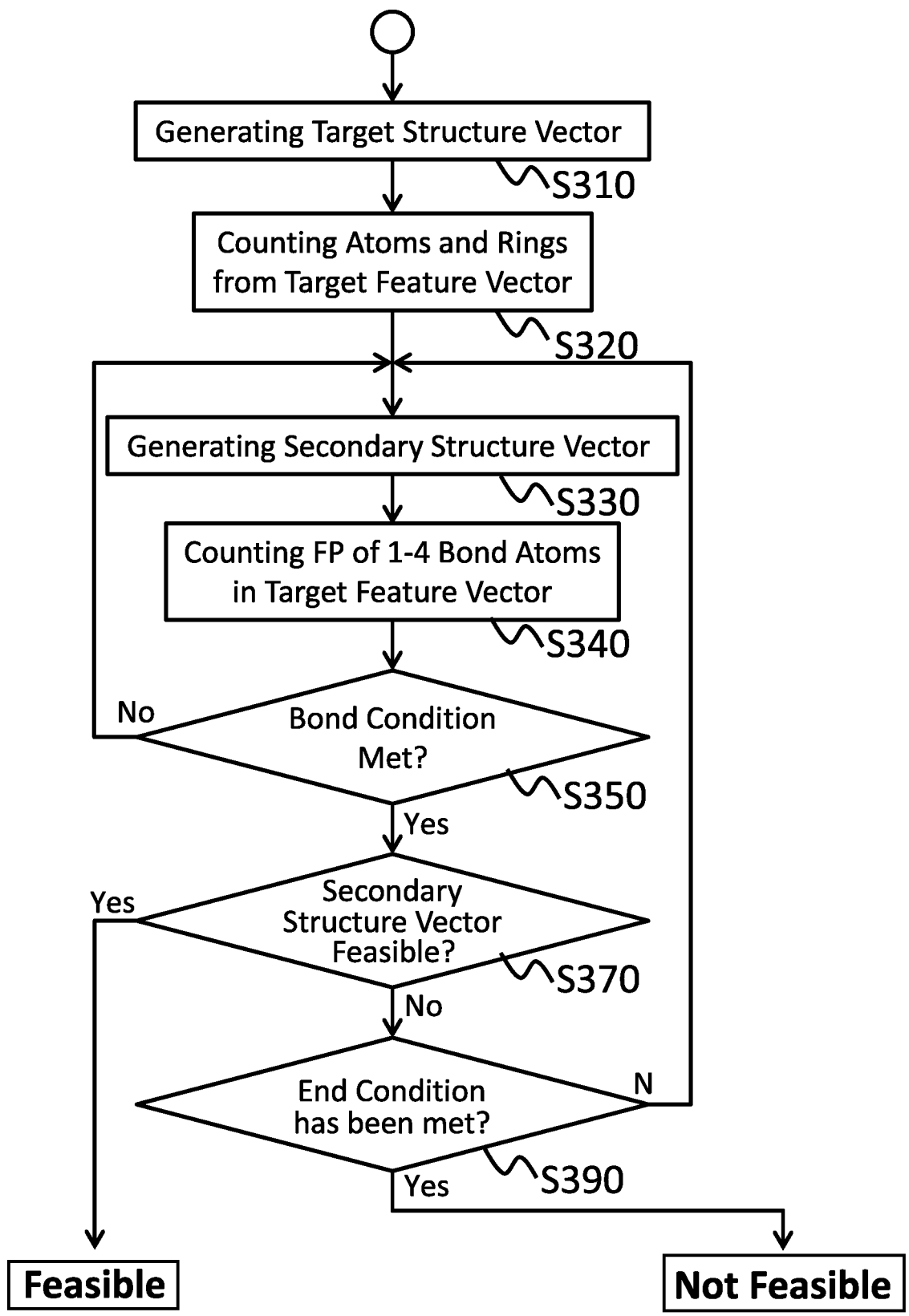
FIG. 15 shows a sub-flow of S300 in the flow of FIG. 3 according to an embodiment of the present invention.

FIG. 15 shows a sub-flow of S300 in the flow of FIG. 3 according to an embodiment of the present invention. An apparatus such as the apparatus 10 may perform operations of S310-S390 of FIG. 15 at the operation S300 of FIG. 3.

At S310, a generating section such as the generating section 120 may generate a target structure vector from the feature vector of the molecule candidate, obtained at S200. In an embodiment, the generating section may count, as $x_1$, the number of atoms classified as the $x_1$ node in FIG. 7 in the molecule candidate by using at least a part of the feature vector (e.g., the data-driven feature section 410).

In the embodiment, the generating section may count, as $x_1$, the number of atoms classified as the x1 node in substructures shown in the data-driven feature section 410. For example, when the data-driven feature section 410 of the molecule candidate indicates that the molecule candidate includes 15 $x_1$ nodes, the generating section may count 15 as $x_1$.

The generating section may also count, as $x_2$, the number of atoms classified as the x2 node in the molecule candidate by using at least a part of the feature vector (e.g., the data-driven feature section 410). The generating section may also count, as $x_3$, the number of atoms classified as the $x_3$ node in the molecule candidate by using at least a part of the feature vector (e.g., the data-driven feature section 410).

The generating section may also count, as $x_4$, the number of atoms classified as the x4 node in the molecule candidate by using at least a part of the feature vector (e.g., the data-driven feature section 410). Thereby, the generating section may obtain a vector $(x_1, x_2, x_3, x_4)$ as the target structure vector.

At S320, an acquiring section such as the acquiring section 130 may acquire a number of atoms and a number of rings of the molecule candidate from the feature vector of the molecule candidate. In an embodiment, the acquiring section may calculate the number of atoms by calculating a sum of the number of atoms listed in the target feature vector (e.g., a sum of C, N, O, S, F, P, Cl, etc), without hydrogen.

In an embodiment, the acquiring section may obtain the number of atoms and/or the number of rings directly from the target feature vector. In such embodiment, the number of atoms and/or the number of rings may be preliminarily defined by a user of the apparatus. For example, the user initially set optimal numbers of atoms/rings for the molecule candidate. In an embodiment, the target feature vector may include the optimal numbers of the atoms/rings. In another embodiment, the acquiring section may obtain the optimal numbers as the number of atoms/rings directly from the user.

In an embodiment, the acquiring section may calculate the number of rings by calculating a sum of the number of rings listed in the target feature vector (e.g., 5-membered ring, 6-membered ring, aromatic ring, etc.). In an embodiment, the acquiring section may obtain the number of rings directly from the target feature vector.

After S320, the apparatus may iterate operations of S330-S390 until an end condition has met.

At S330, the generating section may generate a secondary structure vector that is equal to or larger than the target structure vector. The secondary structure vector ($y_1$, $y_2$, $y_3$, $y_4$) meets ($y_1$, $y_2$, $y_3$, $y_4$)>=($x_1$, $x_2$, $x_3$, $x_4$).

The generating section may generate different secondary structure vectors during the iterations of S330-S390. In an embodiment, the generating section may generate different secondary structure vectors such that the secondary structure vectors gradually become large starting from the target structure vector.

For example, the generating section may use the target structure vector itself ($x_1$, $x_2$, $x_3$, $x_4$) as a secondary structure vector ($y_1$, $y_2$, $y_3$, $y_4$) at a first operation of S330. In the example, as a secondary structure vector ($y_1$, $y_2$, $y_3$, $y_4$), the generating section may generate ($x_1+1$, $x_2$, $x_3$, $x_4$) at a second operation of S330, generate ($x_1$, $x_2+1$, $x_3$, $x_4$) at a third operation of S330, generate ($x_1$, $x_2$, $x_3+1$, $x_4$) at a fourth operation of S330, generate ($x_1$, $x_2$, $x_3$, $x_4+1$) at a fifth operation of S330, generate ($x_1+1$, $x_2+1$, $x_3$, $x_4$) at a sixth operation of S330.

At S340, the acquiring section may acquire a number of atoms of the molecule candidate for each valence, from the target feature vector. In an embodiment, the acquiring section may acquire a number of atoms having 1 bond (e.g., Chlorine (Cl), Fluorine (F), . . . ) from at least a part of the target feature vector (e.g., the pre-defined building component counts section 420), as $L_1$.

Similarly the acquiring section may acquire a number of atoms having 2 bonds (e.g., Oxygen (O), Sulfur (S), . . . ) as $L_2$, a number of atoms having 3 bonds (e.g., Nitrogen (N), . . . ) as $L_3$, a number of atoms having 4 bonds (e.g., Carbon (C), Silicon (Si), . . . ) as $L_4$, from at least the part of the target feature vector (e.g., the pre-defined building component counts section 420). Thereby, the acquiring section may obtain a vector ($L_1$, $L_2$, $L_3$, $L_4$) as a valence-based structure vector.

At S350, a determining section such as the determining section 150 may determine whether the secondary structure vector ($y_1$, $y_2$, $y_3$, $y_4$) meets a bond condition. In an embodiment, the determining section may determine whether the secondary structure vector ($y_1$, $y_2$, $y_3$, $y_4$) meets following 4 conditions:

Condition 1: $y_1 >= L_1$;
Condition 2: $y_1+y_2 >= L_1+L_2$;
Condition 3: $y_1+y_2+y_3 >= L_1+L_2+L_3$;
Condition 4: $y_1+y_2+y_3+y_4 >= L_1+L_2+L_3+L_4$.

In response that the determining section determines that a bond condition is met, the apparatus may proceed with an operation of S370. Otherwise, the apparatus may go back to the operation of S330.

At S370, the determining section may determine whether the secondary structure vector generated at the most recent S330 whether the secondary structure vector is included in a preliminary defined space corresponding to the number of atoms and the number of rings counted at S320. In an embodiment, the preliminary defined space may be included in the structure vectors stored at S100 as shown in FIG. 12.

In an embodiment where the number of atoms and the number of rings counted at S320 is $A_T$ and $R_T$, and the most recent secondary structure vector is represented as ($y_1$, $y_2$, $y_3$, $y_4$), the enumerating section may determine whether a table including the structure vector stored at S100 (such as shown in FIG. 12), includes a record of the number of atoms $A_T$, the number of rings $R_T$, and a structure vector ($y_1$, $y_2$, $y_3$, $y_4$).

If the determining section finds the record, the determining section may determine that the molecule structure of the molecule candidate is feasible and may end the operation of S300. If the determining section does not find the record, then the determining section may proceed with an operation of S390.

At S390, the determining section may determine whether an end condition has been met or not. In an embodiment, the end condition may be that a predetermined number of the secondary structure vectors has been generated at the iterations of S330, that a predetermined range of the secondary structure vectors (e.g., a range of ($x_1$, $x_2$, $x_3$, $x_4$) to ($x_1+10$, $x_2+10$, $x_3+10$, $x_4+10$)) has been generated at the iterations of S330, a predetermined amount of time has passed, etc.

In response to determining that the end condition has not been met, the determining section may go back to the operation of S330 to generate a new secondary structure vector. In response to determining that the end condition has been met, the determining section may end the operation of S300. In this case, the molecule candidate can be regarded as infeasible. After determining feasible or infeasible, the determining section may provide a regressor with a result of the determination.

In the embodiments explained in relation to FIG. 15, the apparatus determines the feasibility by generating the secondary structure vectors. In other embodiments, the determining section may determine the feasibility by determining whether the preliminary defined space includes ($y_1$, $y_2$, $y_3$, $y_4$) that satisfies ($y_1$, $y_2$, $y_3$, $y_4$)>=($x_1$, $x_2$, $x_3$, $x_4$). In the embodiments, ($y_1$, $y_2$, $y_3$, $y_4$) may further satisfy the bond condition such as one explained in relation to S350. The determining section may determine that the molecule candidate is feasible in response to finding at least one ($y_1$, $y_2$, $y_3$, $y_4$). Otherwise, the determining section may determine that the molecule candidate is infeasible.

According to the embodiments explained above, the apparatus may determine whether a feature vector of a molecule candidate is feasible or not based on a target structure vector from the feature vector. In principle, a molecule having a specific number of atoms and rings should have a structure vector within a specific space (e.g., the preliminary defined space such as shown in FIG. 12). Accordingly, the apparatus may determine the feasibility of the molecule candidate based on whether the target structure vector (and secondary vector thereof) of the molecule candidate is included in the preliminary defined space.

During the feature vector search in the frame work shown in FIG. 1, a feature vector of the infeasible molecule candidate can be eliminated from the search space. Thereby, the apparatus may reduce computational resources and/or time for finding promising molecules.

In some cases, the target structure vector may not be identical to a structure vector obtained by a molecule candidate. By using not only the target structure vector itself but also the secondary structure vectors as explained in relation to FIG. 15, the apparatus may more precisely determine feasibility of the molecule candidate. The apparatus may further exactly determine feasibility of the molecule candidate by using the bond condition of the molecule candidate as explained in relation to FIG. 15.

Various embodiments of the present invention may be described with reference to flowcharts and block diagrams whose blocks may represent (1) steps of processes in which operations are performed or (2) sections of apparatuses responsible for performing operations. Certain steps and sections may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server.

In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 16:
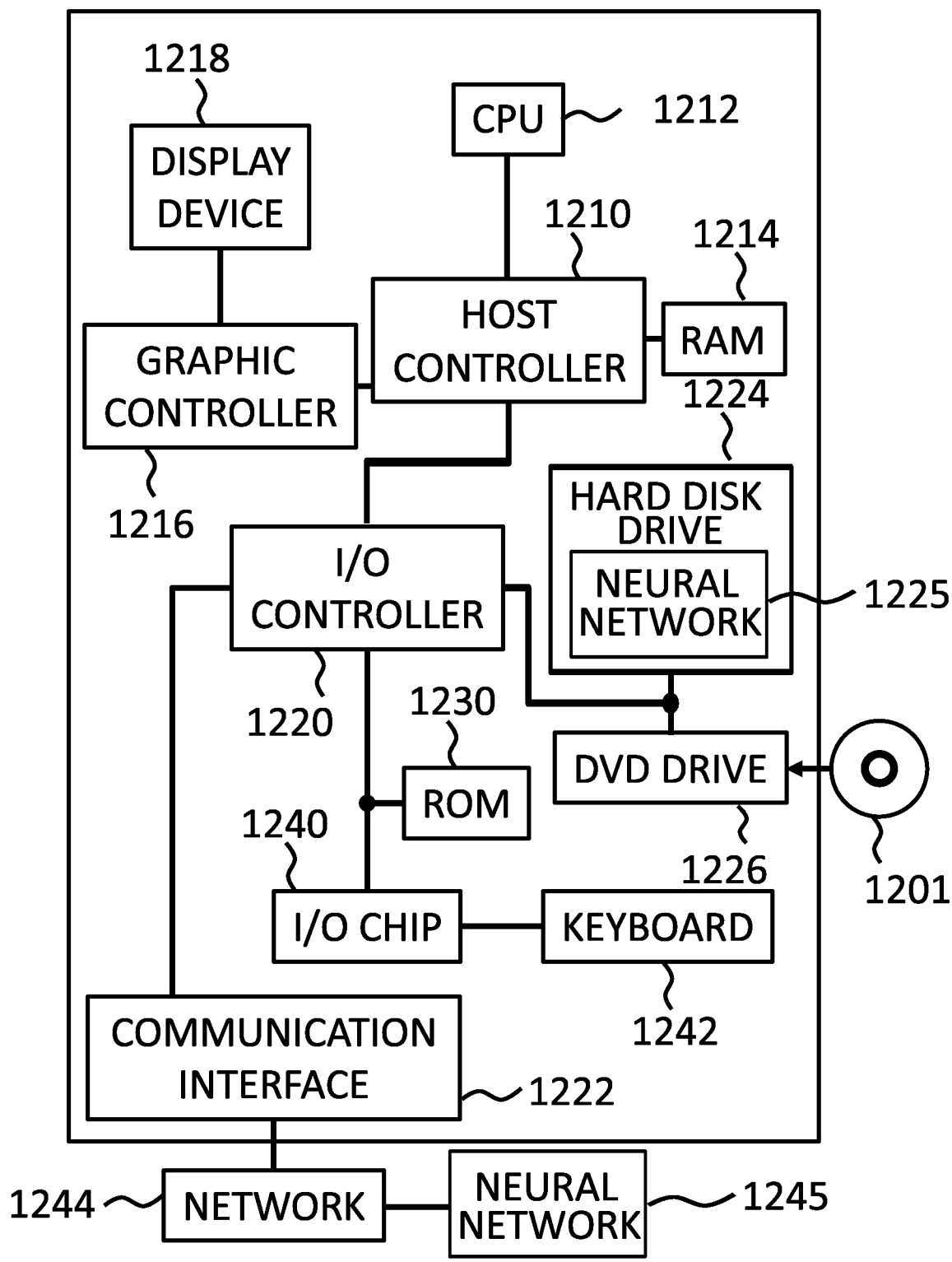
FIG. 16 shows an exemplary hardware configuration of a computer that functions as a system, according to an embodiment of the present invention.

FIG. 16 shows an example of a computer 1200 in which aspects of the present invention may be wholly or partly embodied. A program that is installed in the computer 1200 can cause the computer 1200 to function as or perform operations associated with apparatuses of the embodiments of the present invention or one or more sections thereof, and/or cause the computer 1200 to perform processes of the embodiments of the present invention or steps thereof. Such a program may be executed by the CPU 1212 to cause the computer 1200 to perform certain operations associated with some or all of the blocks of flowcharts and block diagrams described herein.

The computer 1200 according to the present embodiment includes a CPU 1212, a RAM 1214, a graphics controller 1216, and a display device 1218, which are mutually connected by a host controller 1210. The computer 1200 also includes input/output units such as a communication interface 1222, a hard disk drive 1224, a DVD-ROM drive 1226 and an IC card drive, which are connected to the host controller 1210 via an input/output controller 1220. The computer also includes legacy input/output units such as a ROM 1230 and a keyboard 1242, which are connected to the input/output controller 1220 through an input/output chip 1240.

The CPU 1212 operates according to programs stored in the ROM 1230 and the RAM 1214, thereby controlling each unit. The graphics controller 1216 obtains image data generated by the CPU 1212 on a frame buffer or the like provided in the RAM 1214 or in itself, and causes the image data to be displayed on the display device 1218.

The communication interface 1222 communicates with other electronic devices via a network 1244. The hard disk drive 1224 stores programs and data used by the CPU 1212 within the computer 1200. The DVD-ROM drive 1226 reads the programs or the data from the DVD-ROM 1201, and provides the hard disk drive 1224 with the programs or the data via the RAM 1214. The IC card drive reads programs and data from an IC card, and/or writes programs and data into the IC card. In some embodiments, the neural network 1225 can be stored on hard disk drive 1124. The computer 1200 can train the neural network 1245 stored on the hard disk drive 1224.

The ROM 1230 stores therein a boot program or the like executed by the computer 1200 at the time of activation, and/or a program depending on the hardware of the computer 1200. The input/output chip 1240 may also connect various input/output units via a parallel port, a serial port, a keyboard port, a mouse port, and the like to the input/output controller 1220.

A program is provided by computer readable media such as the DVD-ROM 1201 or the IC card. The program is read from the computer readable media, installed into the hard disk drive 1224, RAM 1214, or ROM 1230, which are also examples of computer readable media, and executed by the CPU 1212. The information processing described in these programs is read into the computer 1200, resulting in cooperation between a program and the above-mentioned various types of hardware resources. An apparatus or method may be constituted by realizing the operation or processing of information in accordance with the usage of the computer 1200.

For example, when communication is performed between the computer 1200 and an external device, the CPU 1212 may execute a communication program loaded onto the RAM 1214 to instruct communication processing to the communication interface 1222, based on the processing described in the communication program. The communication interface 1222, under control of the CPU 1212, reads transmission data stored on a transmission buffering region provided in a recording medium such as the RAM 1214, the hard disk drive 1224, the DVD-ROM 1201, or the IC card, and transmits the read transmission data to a network 1244 or writes reception data received from a network 1244 to a reception buffering region or the like provided on the recording medium.

In addition, the CPU 1212 may cause all or a necessary portion of a file or a database to be read into the RAM 1214, the file or the database having been stored in an external recording medium such as the hard disk drive 1224, the DVD-ROM drive 1226 (DVD-ROM 1201), the IC card, etc., and perform various types of processing on the data on the RAM 1214. The CPU 1212 may then write back the processed data to the external recording medium.

Various types of information, such as various types of programs, data, tables, and databases, may be stored in the recording medium to undergo information processing. The CPU 1212 may perform various types of processing on the data read from the RAM 1214, which includes various types of operations, processing of information, condition judging, conditional branch, unconditional branch, search/replace of information, etc., as described throughout this disclosure and designated by an instruction sequence of programs, and writes the result back to the RAM 1214. In addition, the CPU 1212 may search for information in a file, a database, etc., in the recording medium. For example, when a plurality of entries, each having an attribute value of a first attribute associated with an attribute value of a second attribute, are stored in the recording medium, the CPU 1212 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-explained program or software modules may be stored in the computer readable media on or near the computer 1200. In addition, a recording medium such as a hard disk or a RAM provided in a server system connected to a dedicated communication network 1244 or the Internet can be used as the computer readable media, thereby providing the program to the computer 1200 via the network 1244. In some embodiments, the computer 1200 can communicate with a neural network 1245 over the network 1244. The computer 1200 can train the neural network 1245 over the network 1244. The neural network 1245 can be embodiment as one or more nodes.

While the embodiments of the present invention have been described, the technical scope of the invention is not limited to the above described embodiments. It will be apparent to persons skilled in the art that various alterations and improvements can be added to the above-described embodiments. It should also apparent from the scope of the claims that the embodiments added with such alterations or improvements are within the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A computer-implemented method for neural network training, comprising:
generating a target structure vector that represents numbers of a plurality of partial structures, from a feature vector of a molecule candidate; and
determining whether a molecule structure of the molecule candidate is feasible by using at least the target structure vector.

2. The method of claim 1, wherein the plurality of partial structures includes structures having different numbers of edges connected to a node.

3. The method of claim 2, wherein the plurality of partial structures includes:
a first structure having one edge connected to the one node,
a second structure having two edges connected to the one node,
a third structure having three edges connected to the one node, and
a fourth structure having four edges connected to the one node.

4. The method of claim 1, wherein the feature vector includes an indication of whether the molecule candidate includes one or more unit structures.

5. The method of claim 4, wherein the feature vector indicates a number of atoms and a number of rings in the molecule candidate.

6. The method of claim 1, further comprising:
acquiring a number of atoms and a number of rings of the molecule candidate from the feature vector of the molecule candidate,
wherein the determining whether a molecule structure of the molecule candidate is feasible by using at least the target structure vector is performed by further using the number of atoms and the number of rings of the molecule candidate.

7. The method of claim 6, wherein the determining whether a molecule structure of the molecule candidate is feasible by using at least the target structure vector, includes:
determining that the molecule structure of the molecule candidate is feasible in response to the target structure vector being included in a preliminary defined space that corresponds to the number of atoms and the number of rings of the molecule candidate.

8. The method of claim 6, further comprising:
generating one or more secondary structure vectors that is equal to or larger than the target structure vector,
wherein the determining whether a molecule structure of the molecule candidate is feasible by using at least the target structure vector is performed by further using the one or more secondary structure vectors.

9. The method of claim 6, further comprising:
acquiring a number of atoms of the molecule candidate for each valence, from the feature vector of the molecule candidate,
wherein the determining whether a molecule structure of the molecule candidate is feasible by using at least the target structure vector is performed by further using the number of atoms of the molecule candidate for each valence.

10. The method of claim 7, further comprising:
enumerating feasible structure vectors for each pair of the number of nodes and rings,
wherein the preliminary defined space that corresponds to the number of nodes and the number of rings of the molecule candidate is defined by the enumerated feasible structure vectors.

11. The method of claim 10, wherein the enumerating feasible structure vectors for each pair of the number of nodes and rings, includes:
growing a graph,
counting the number of nodes and the number of rings of the graph, and
storing a structure vector of the graph for a pair of the counted number of nodes and the counted number of rings of the graph.

12. The method of claim 11, wherein the growing a graph, comprises at least one of:
adding a new node to the graph, and
forming a new ring in the graph.

13. An apparatus comprising
a processor; and
one or more computer readable mediums collectively including instructions that, when executed by the processor, cause the processor to perform operations including:
generating a target structure vector that represents numbers of a plurality of partial structures, from a feature vector of a molecule candidate; and
determining whether a molecule structure of the molecule candidate is feasible by using at least the target structure vector.

14. The method of claim 13, wherein the plurality of partial structures include structures having different numbers of edges connected to a node.

15. The method of claim 14, wherein the plurality of partial structures includes:
a first structure having one edge connected to the one node,
a second structure having two edges connected to the one node,
a third structure having three edges connected to the one node, and
a fourth structure having four edges connected to the one node.

16. The method of claim 13, wherein the feature vector includes an indication of whether the molecule candidate includes one or more unit structures.

17. The method of claim 16, wherein the feature vector indicates a number of atoms and a number of rings in the molecule candidate.

18. The method of claim 13, wherein the operations further comprise:
acquiring a number of atoms and a number of rings of the molecule candidate from the feature vector of the molecule candidate,
wherein the determining whether a molecule structure of the molecule candidate is feasible by using at least the target structure vector is performed by further using the number of atoms and the number of rings of the molecule candidate.

19. The method of claim 18, wherein the determining whether a molecule structure of the molecule candidate is feasible by using at least the target structure vector, includes:
determining that the molecule structure of the molecule candidate is feasible in response to the target structure vector being included in a preliminary defined space that corresponds to the number of atoms and the number of rings of the molecule candidate.

20. A computer program product including one or more computer readable storage mediums collectively storing program instructions that are executable by a processor to cause the processor to perform operations comprising:
generating a target structure vector that represents numbers of a plurality of partial structures, from a feature vector of a molecule candidate; and
determining whether a molecule structure of the molecule candidate is feasible by using at least the target structure vector.

21. The computer program product of claim 20, wherein the plurality of partial structures include structures having different numbers of edges connected to a node.

22. The computer program product of claim 21, wherein the plurality of partial structures includes:
a first structure having one edge connected to the one node,
a second structure having two edges connected to the one node,
a third structure having three edges connected to the one node, and
a fourth structure having four edges connected to the one node.

23. The computer program product of claim 20, wherein the feature vector includes an indication of whether the molecule candidate includes one or more unit structures.

24. The computer program product of claim 23, wherein the feature vector indicates a number of atoms and a number of rings in the molecule candidate.

25. The computer program product of claim 20, wherein the operations further comprise:
acquiring a number of atoms and a number of rings of the molecule candidate from the feature vector of the molecule candidate,
wherein the determining whether a molecule structure of the molecule candidate is feasible by using at least the target structure vector is performed by further using the number of atoms and the number of rings of the molecule candidate.

* * * * *